US011833252B2

(12) United States Patent
Quadir et al.

(10) Patent No.: US 11,833,252 B2
(45) Date of Patent: Dec. 5, 2023

(54) AQUEOUS ENTERIC COATING COMPOSITION

(71) Applicants: SE Tylose USA, Inc., Plaquemine, LA (US); Shin-Etsu Chemical Co., Ltd., Yokohama (JP)

(72) Inventors: Anisul Quadir, East Setauket, NY (US); Sakae Obara, Fort Lee, NJ (US)

(73) Assignee: SE Tylose USA, Inc., Plaquemine, LA (US)

( * ) Notice: Subject to any disclaimer, the term of this patent is extended or adjusted under 35 U.S.C. 154(b) by 722 days.

(21) Appl. No.: 17/001,152

(22) Filed: Aug. 24, 2020

(65) Prior Publication Data

US 2020/0383925 A1    Dec. 10, 2020

Related U.S. Application Data

(63) Continuation of application No. 15/132,627, filed on Apr. 19, 2016, now abandoned.

(60) Provisional application No. 62/160,203, filed on May 12, 2015.

(51) Int. Cl.
*A61K 9/28* (2006.01)
*A61K 9/50* (2006.01)

(52) U.S. Cl.
CPC ............ *A61K 9/282* (2013.01); *A61K 9/2866* (2013.01); *A61K 9/5015* (2013.01); *A61K 9/5042* (2013.01)

(58) Field of Classification Search
CPC ..... A61K 9/282; A61K 9/2866; A61K 9/5015
USPC ...................................................... 106/170.1
See application file for complete search history.

(56) References Cited

U.S. PATENT DOCUMENTS

| | | | |
|---|---|---|---|
| 6,139,875 A | 10/2000 | Adams et al. | |
| 7,498,309 B2 | 3/2009 | Levy | |
| 8,147,871 B2 | 4/2012 | Brown et al. | |
| 8,361,498 B2 | 1/2013 | McAllister et al. | |
| 8,580,302 B2 | 11/2013 | Dittmar et al. | |
| 8,980,314 B2 | 3/2015 | Ding et al. | |
| 9,011,926 B2 | 4/2015 | Nagahara et al. | |
| 2005/0214331 A1* | 9/2005 | Levy | A61K 47/44 514/3.8 |
| 2010/0316709 A1 | 12/2010 | Kurasawa et al. | |
| 2011/0217426 A1 | 9/2011 | Perry et al. | |
| 2012/0244219 A1 | 9/2012 | Lahav et al. | |
| 2012/0322851 A1* | 12/2012 | Hardee | A61K 9/0053 514/44 R |
| 2013/0243872 A1 | 9/2013 | Kim et al. | |
| 2013/0295188 A1* | 11/2013 | Cade | A61K 47/10 424/494 |

FOREIGN PATENT DOCUMENTS

EM     0008780 B1     3/1980
WO     2005074395 A2  8/2005

OTHER PUBLICATIONS

Extended European Search Report for EP Application No. 16793160.9 based on PCT/US2016/029514, dated Nov. 18, 2018.
The International Bureau of WIPO, International Preliminary Report on Patentability based on PCT/US2016/029514, dated Nov. 14, 2017.
Cellulose & Pharmaceutical Excipients Department of Shin-Etsu, Shin-Etsu AQOAT, Entericceating agent, Solid dispersion carrier, pp. 1-18, published Jul. 2014, Japan.
International Search Report and Written Opinion of the International Search Authority for PCT/US16/29514, dated Jul. 11, 2016.
Korean Intellectual Property Office, Office Action for Korean Patent Application No. 10-2017-7032322, dated Dec. 23, 2022.

* cited by examiner

*Primary Examiner* — Douglas B Call

(74) *Attorney, Agent, or Firm* — Williams Mullen; Michael Sajovec

(57) ABSTRACT

An aqueous enteric coating composition including hydroxypropylmethylcellulose, acetate succinate, and a basic amino acid.

4 Claims, No Drawings

AQUEOUS ENTERIC COATING COMPOSITION

CROSS-RELATED APPLICATION DATA

This application claims priority to U.S. application Ser. No. 15/132,627 filed Apr. 19, 2016 now abandoned, which claims priority to U.S. Provisional Application No. 62/160,203 filed May 12, 2015, the disclosures of which are incorporated herein by reference in their entireties.

FIELD OF THE INVENTION

The present invention relates to an aqueous enteric coating composition with improved processability.

BACKGROUND OF THE INVENTION

Enteric coatings are used on various tablets or pellets utilized to orally deliver a wide range of pharmaceuticals and nutraceuticals. Enteric coatings are typically applied to protect the pharmaceutical or nutraceutical being delivered from the acid pH of the stomach. Most enteric coatings comprise one or more of hydroxypropylmethylcellulose phthalate, cellulose acetate phthalate, carboxymethylethylcellulose, methyl methacrylate-methacrylate copolymer, methacrylate-ethyl acrylate copolymer, methacrylate-methyl acrylate-methyl methacrylate copolymer, hydroxypropylmethylcellulose acetate succinate, polyvinyl acetate phthalate and shellac.

One particular enteric coating composition is based on hydroxypropylmethylcellulose acetate succinate (HPMCAS) available as Shin-Etsu AQOAT® from Shin-Etsu Chemical Co., Ltd. (Japan). Existing coating methods utilizing HPMCAS, however, have some processing difficulties. There is a significant problem with respect to nozzle clogging in the spray apparatus. One solution is to cool the coating fluid to a temperature less than 10° C. and to reduce polymer concentration to less than 7 percent. Other solutions include suspending the HPMCAS in ammonia or to dissolve it in a solvent such as ethanol or acetone. Use of ammonia or solvents may be difficult to handle for large scale commercial purposes, as there are stability issues and potential environmental and safety issues. Other options are to use a special dual spray nozzle or to use a powder nozzle. These options require a significant capital investment in the spray technology.

SUMMARY OF THE INVENTION

The present invention aims to overcome the above problems and difficulties with an aqueous enteric coating composition that does not cause clogging in spray nozzles, avoids the use of ammonia or solvents and does not require expensive nozzle or spray technology.

The aqueous enteric coating composition comprises hydroxypropylmethylcellulose acetate succinate and a basic amino acid. In one embodiment, the aqueous enteric coating composition comprises 5 to 20 percent hydroxypropylmethylcellulose acetate succinate, 0.05 to 1.0 percent L-arginine or L-histidine, 0.5 to 10 percent plasticizer, 0.1 to 10 percent anti-tacking agent, 0.05 to 0.5 percent surfactant, and 65 to 95 percent water.

DETAILED DESCRIPTION OF EMBODIMENTS OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

The term "consists essentially of" (and grammatical variants), as applied to the methods in this invention, means the methods or compositions can contain additional steps as long as the additional steps or components do not materially alter the basic and novel characteristic(s) of the present invention.

The term "consisting of" excludes any additional step that is not specified in the claim.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

All patents, patent applications and publications referred to herein are incorporated by reference in their entirety. In case of a conflict in terminology, the present specification is controlling.

As one of ordinary skill in the art may appreciate, the parameters described herein may vary greatly depending on the process, and/or formulation as well as the desired properties of the final product.

The present invention is directed to a novel aqueous enteric coating composition comprising hydroxypropylmethylcellulose acetate succinate (HPMCAS), a basic amino acid and additives such as plasticizers, surfactants, anti-tacking agents and the like.

In one embodiment, the HPMCAS is Shin-Etsu AQOAT® available from Shin-Etsu Chemical Co., Ltd. (Japan). Optionally, other enteric coating materials may be included. Exemplary other materials include hydroxypropylmethylcellulose phthalate, cellulose acetate phthalate, carboxymethylethylcellulose, methyl methacrylate-methacrylate copolymer, methacrylate-ethyl acrylate copolymer, methacrylate-methyl acrylate-methyl methacrylate copolymer, hydroxypropylmethylcellulose acetate succinate, polyvinyl acetate phthalate and shellac. Often such materials are included to allow the overall enteric coating to dissolve at different rates based on different pHs. The amount of HPMCAS in the composition may be from about 5 to about 20 percent by weight of the composition.

Suitable basic amino acids include one or more of L-arginine, L-histidine and L-lysine. The amount of basic amino acid in the composition may be from about 0.05 percent to about 1.0 percent by weight of the composition.

Plasticizers are added to assist in the melting characteristics of the composition. Exemplary of plasticizers that may be employed in this invention are triethyl citrate (TEC), triacetin, tributyl citrate, acetyl triethyl citrate (ATEC), acetyl tributyl citrate (ATBC), dibutyl phthalate, dibutyl sebacate (DBS), diethyl phthalate, vinyl pyrrolidone glycol triacetate, polyethylene glycol, polyoxyethylene sorbitan monolaurate, propylene glycol, propylene carbonate or castor oil; and combinations or mixtures thereof. The amount of plasticizers in the composition may be from about 0.5 to about 10 percent by weight of the composition.

Surfactants are added to modify surface characteristics of the coated material and include Pluronics® (block copolymers of ethylene oxide and propylene oxide), lecithin, Aerosol OT® (sodium dioctyl sulfosuccinate), sodium lauryl sulfate, Polyoxyl 40™ hydrogenated castor oil, polyoxyethylene sorbitan fatty acid esters, i.e., the polysorbates such as Tween®, such as Tween 20, 60 & 80, the sorbitan fatty acid esters, i.e., sorbitan monolaurate, monooleate, monopalmitate, monostearate, etc. such as Span® or Arlacel®, Emsorb®, Capmul®, or Sorbester®, Triton X-200, polyethylene glycol's, glyceryl monostearate, Vitamin E-TPGS® (d-alpha-tocopheryl polyethylene glycol 1000 succinate), sucrose fatty acid esters, such as sucrose stearate, sucrose oleate, sucrose palmitate, sucrose laurate, and sucrose acetate butyrate, and combinations and mixtures thereof. Preferred surfactants are Vitamin E-TPGS®, sodium lauryl sulfate, sucrose fatty acid esters, lecithin, and the Pluronic groups. The amount of surfactant in the composition may be from about 0.05 to about 0.5 percent by weight of the composition.

Anti-tacking agents or processing lubricants may be included. Exemplary agents and lubricants include stearyl alcohol, stearic acid, glycerol monostearate (GMS), talc, magnesium stearate, silicon dioxide, amorphous silicic acid, and fumed silica; and combinations or mixtures thereof. The amount of anti-tacking agent or processing lubricant may be from about 0.1 percent to about 10 percent by weight of the composition.

The overall composition may include about 65 to about 95 percent by water weight as the dispersing agent to provide the composition in aqueous form.

Other additives may include absorption enhancers, dissolution modifying agents, coloring aids, flavoring agents, and stabilizing agents (e.g., dibasic sodium phosphate).

The aqueous enteric coating composition may be used on tablets, pellets, granules, hard and soft capsules to deliver pharmaceuticals and nutraceuticals.

As used herein "pharmaceutical" is defined as any chemical substance intended for use in the medical diagnosis, cure, treatment, or prevention of disease, for example over-the-counter drugs (OTC) and prescription only medicine (POM). Exemplary active pharmaceutical components are listed in U.S. Pat. No. 6,723,358, column 9, line 25 to column 13, line 25, the disclosure of which is incorporated herein by reference in its entirety.

As used herein "nutraceutical" supplement include any nutrients that may provide health and medical benefits, including the prevention and treatment of disease. Examples include, but are not limited to, vitamins, minerals, probiotics, enzymes, herb and other botanical extracts, amino acid, concentrates, metabolites, constituents, etc.

Exemplary vitamins and minerals include, but are not limited to, vitamins A (in the form of, for example, palmitate or beta carotene), B-complex (such as B-1, B-2, B-6 and B-12), C, D, E and K; niacin; acid vitamins such as pantothenic acid and folic acid; biotin; minerals such as iron, calcium, magnesium, iodine, copper, phosphorus, zinc, manganese, potassium, chromium, cobalt, molybdenum, selenium, nickel, tin, silicon, vanadium and boron; nutraceutical supplements such as fluorine and chlorine; and the like. Various herbs and herbal remedies may be utilized as the nutraceutical supplements. The herbs are generally selected from those which have various medicinal or dietary supplement properties. Herbs are generally aromatic plants or plant parts that can be used medicinally or for flavoring. Examples include Gingko biloba, gotu kola, echinacea, St. John's wort, ginseng, valerian and the like. Suitable herbs may be used alone or in various mixtures in the filling described herein.

The present invention will be further illustrated by the following non-limiting examples.

EXAMPLES

Example 1

A stock solution of L-histidine was prepared by dissolving 3 g in 100 ml water. The pH of the solution was 7.47. The following formulation was prepared and evaluated:
Conventional Formulation (No Amino Acid)

| HPMCAS (AS-MF) | 7 (wt %) |
|---|---|
| TEC (Triethyl citrate) | 2.1 |
| Talc | 2.1 |
| SLS (Sodium lauryl sulfate) | 0.2 |
| Water | ad 100 (Final wt 600 g) |

SLS was dissolved in water. HPMCAS was then dispersed in a same amount of water. Talc was dispersed in a separate container and pass through high shear homogenizer as described earlier and then added to the above dispersion and mixed for another 30 minute. TEC was then added to the above dispersion and mixed for 30 minutes
Formulation

| HPMCAS (AS-MF) | 10 (wt %) |
|---|---|
| L-histidine | 0.03 |
| TEC (Triethyl citrate) | 3.0 |
| Talc | 2.5 |
| SLS (Sodium lauryl sulfate) | 0.3 |
| Water | ad 100 (Final wt 600 g) |

SLS was dissolved in water. HPMCAS was then dispersed in a same amount of water. The L-histidine solution was added to the above dispersion slowly to increase the pH (target 5.6 to 5.8). After adding 100 ml the pH was measured as 5.3. Talc was dispersed in a separate container and pass through high shear homogenizer as described earlier and then added to the above dispersion and mixed for another 30 minute. TEC was then added to the above dispersion and mixed for 30 minutes.

Results:
Coagulation Behavior

The coating dispersion was passed through a 60 mesh screen. The conventional formulation showed coagulation at room temperature and a considerably amount of aggregated mass are remaining on the screen. The Formulation of Example 1 showed no coagulation was remaining mass on the screen was minimal.

The coating experiment was also performed using:
Equipment: A table-top side-vented pan coater (Glatt GMPC-I, batch size: 500 g)
Core tablets: Placebo tablets (prepared mainly from lactose and cornstarch)

| Machine | GLATT Mini Coater GMPC1 |
|---|---|
| Pan Size | 0.8 L |
| Charge | 500 g |
| Inlet Temperature | 50-55° C. |
| Outlet Temperature | 33-36° C. |
| Air flow | 1.0 m³/min |
| Spray feed rate | 3.5-4.5 g/min |
| Atomizing pressure | 100 kPa |
| Nozzle diameter | 0.8 mm |
| Distance | 10 cm |
| Pan speed | 7-13 rpm |
| Post drying | 30-60 min. at 55° C. (inlet) |

With the conventional formulation, the coating could not be performed due to the coagulation at room temperature. Using Formulation A, the coating went well without nozzle clogging.

Example 2

Another amino acid L-arginine was used as stabilizer. 10 g of L-arginine was dissolved in 100 mL water as a stock solution.
Formulation

| HPMCAS (AS-MF) | 10 (wt %) |
|---|---|
| L-arginine | 0.33 |
| TEC | 2.5 |
| Talc | 3.0 |
| SLS | 0.3 |
| Water | ad 100 (Final wt 600 g) |

SLS was dissolved in a required quantity of water. HPMCAS was then added and mix for 60 minutes. Talc was dispersed in a separate container with a high shear homogenizer and then added to the above dispersion and mix for 30 minutes Finally added TEC into the above dispersion and mix for another 60 minutes The pH of the dispersion was 5.08.
Results:
Coagulation Behavior No coagulation was observed.
Coating Experiment (Same as Example 1)

Coating went smoothly without any nozzle clogging. Coating was performed to the weight gain of 13%.
Gastric Resistance Test Six tablets were immersed in USP simulated gastric fluid (pH 1.2, without pepsin) for 1 hr using a disintegration tester. All tablets were intact and the average uptake of gastric fluid (tablet weight gain after the test) was only 4.2%.

Example 3

The loading of HPMCAS was then increased to 12% with the following formulation:

Formulation

| HPMCAS (AS-MF) | 12 (wt %) |
|---|---|
| L-arginine | 0.33 |
| TEC | 3.6 |
| Talc | 3.6 |
| SLS | 0.12 |
| Water | ad 100 (Final wt 600 g) |

Preparation procedure was the same as Example 2.
Results:
Coagulation Behavior

No coagulation was observed.
Coating Experiment (Same as Example 1)

Coating went smoothly without any nozzle clogging. Coating was performed to the weight gain of 14%.
Gastric Resistance Test and its Stability The test method was the same as Example 2. All tablets were intact and the average uptake of gastric fluid (tablet weight gain after the test) was only 4.0%. The tablets were put into accelerated stability test at 40° C./75% RH (closed bottle). The gastric uptake after 4 weeks was only 2.9%.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

Example 4

Coloring agent (titanium oxide) was added:
Formulation

| HPMCAS (AS-MF) | 12 (wt %) |
|---|---|
| L-arginine | 0.33 |
| TEC | 3.6 |
| Talc | 3.6 |
| SLS | 0.25 |
| Titanium Dioxide | 0.5 |
| Water | ad 100 (Final wt 600 g) |

Preparation procedure was the same as Example 2.
Results:
Coagulation Behavior

No coagulation was observed.
Coating Experiment (Same as Example 1)

Coating went smoothly without any nozzle clogging. Coating was performed to the weight gain of 14%.

Example 5

Another coloring agent (iron oxide) was added:

| HPMCAS (AS-MF) | 12 (wt %) |
|---|---|
| L-arginine | 0.33 |
| TEC | 3.6 |
| Talc | 3.6 |
| SLS | 0.25 |
| Iron oxide | 0.5 |
| Water | ad 100 (Final wt 600 g) |

Preparation procedure was the same as Example 2.
Results:
Coagulation Behavior

No coagulation was observed.
Coating Experiment (Same as Example 1)

Coating went smoothly without any nozzle clogging. Coating was performed to the weight gain of 14%.

Example 6

Silicon Dioxide was used as anti-tacking agent:

| | |
|---|---|
| HPMCAS (AS-MF) | 12 (wt %) |
| L-arginine | 0.33 |
| TEC | 3.6 |
| Silicon Dioxide (Aerosil ® R972) | 0.5 |
| SLS | 0.25 |

Preparation procedure was the same as Example 2.
Results:
Coagulation Behavior
 No coagulation was observed.
Coating Experiment (Same as Example 1)
 Coating went smoothly without any nozzle clogging. Coating was performed to the weight gain of 14%.

Example 7

Example of pellet coating:
The formulation was the same as Example 3. The core pellet was cellulose beads.

| Machine | MIDI-GLATT Wurster Coating |
|---|---|
| Charge | 180 g (Celphere CP-507) |
| Inlet Temperature | 42-43° C. |
| Product Temperature | 33-35° C. |
| Air flow | 0.8 m³/min |
| Spray feed rate | 3.3 g/min |
| Atomizing pressure | 100 kPa |
| Spray Nozzle | 0.5 mm |
| Partition Height | 20 mm |
| Retaining Screen | 100 mesh |

Results:
Coagulation Behavior
 No coagulation was observed.
Coating Experiment (Same as Example 1)
 Coating went smoothly without any nozzle clogging. Coating was performed to the weight gain of 30%.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

That which is claimed:

1. An aqueous enteric coating composition comprising:
 a) 5 to 20 percent by weight hydroxypropylmethylcellulose acetate succinate;
 b) 0.05 to 1.0 percent by weight L-arginine and L-histidine;
 c) 0.5 to 10 percent by weight plasticizer;
 d) 0.1 to 10 percent by weight anti-tacking agent;
 e) 0.05 to 0.5 percent by weight surfactant; and
 f) 65 to 95 percent by weight water.

2. The aqueous enteric coating composition according to claim 1, wherein the surfactant is selected from the group consisting of sodium lauryl sulfate, sucrose fatty acid esters, lecithin, and d-alpha-tocopheryl polyethylene glycol, and combinations and mixtures thereof.

3. The aqueous enteric coating composition according to claim 1, wherein the anti-tacking agent is selected from the group consisting of stearyl alcohol, stearic acid, glycerol monostearate (GMS), talc, magnesium stearate, silicon dioxide, amorphous silicic acid, and fumed silica, and combinations or mixtures thereof.

4. A pharmaceutical composition comprising a tablet, pellet, granule, hard capsule or soft capsule coated with the aqueous enteric coating composition of claim 1 and a pharmaceutical or nutraceutical.

\* \* \* \* \*